United States Patent
Ahn et al.

(10) Patent No.: US 10,848,002 B2
(45) Date of Patent: Nov. 24, 2020

(54) MICROROBOT PROPULSION APPARATUS BASED ON WIRELESS POWER TRANSFER INCLUDING MULTIPURPOSE INVERTER AND METHOD OF MANUFACTURING THE SAME

(71) Applicants: KOREA ADVANCED INSTITUTE OF SCIENCE AND TECHNOLOGY, Daejeon (KR); UNIVERSITY-INDUSTRY COOPERATION GROUP OF KYUNG HEE UNIVERSITY, Yongin-si (KR)

(72) Inventors: Seung Young Ahn, Daejeon (KR); Bom Son Lee, Yongin-si (KR); Dong Wook Kim, Daejeon (KR); Hong Kyun Kim, Daejeon (KR); Jae Hyoung Park, Daejeon (KR); Bum Jin Park, Daejeon (KR); Ka Ram Hwang, Daejeon (KR)

(73) Assignees: KOREA ADVANCED INSTITUTE OF SCIENCE AND TECHNOLOGY, Daejeon (KR); UNIVERSITY-INDUSTRY COOPERATION GROUP OF KYUNG HEE UNIVERSITY, Yongin-si (KR)

(*) Notice: Subject to any disclaimer, the term of this patent is extended or adjusted under 35 U.S.C. 154(b) by 107 days.

(21) Appl. No.: 16/209,517

(22) Filed: Dec. 4, 2018

(65) Prior Publication Data
US 2019/0173320 A1   Jun. 6, 2019

(30) Foreign Application Priority Data

Dec. 5, 2017 (KR) .......................... 10-2017-0166206
Jun. 26, 2018 (KR) .......................... 10-2018-0073410

(51) Int. Cl.
*H02J 50/12* (2016.01)
*H02M 7/5387* (2007.01)
(Continued)

(52) U.S. Cl.
CPC .............. *H02J 50/12* (2016.02); *H02M 3/158* (2013.01); *H02M 7/5387* (2013.01);
(Continued)

(58) Field of Classification Search
CPC .......... H02J 50/12; A61B 34/30; A61B 34/73; H02M 3/158; H02M 7/5387
(Continued)

(56) References Cited

U.S. PATENT DOCUMENTS

| 2012/0112553 A1* | 5/2012 | Stoner, Jr. | ............... | H02J 50/70 307/104 |
| 2013/0053767 A1* | 2/2013 | Pivonka | .................. | H02J 50/23 604/95.01 |

FOREIGN PATENT DOCUMENTS

KR   10-2012-0116801 A   10/2012

OTHER PUBLICATIONS

Communication dated Mar. 31, 2020, issued by the Korean Patent Office in counterpart Korean Application No. 10-2018-0073410.

* cited by examiner

*Primary Examiner* — Michael R. Fin
(74) *Attorney, Agent, or Firm* — Sughrue Mion, PLLC (57) ABSTRACT

Disclosed are a microrobot propulsion apparatus based on wireless power transmission and a method of manufacturing the same. The microrobot propulsion apparatus according to one embodiment of the present disclosure may include a coil part for outputting a time-varying magnetic field or a static magnetic field applied to a microrobot including a coil for receiving power and a coil for an electromagnet, and a (Continued)

multipurpose inverter including a static magnetic field path portion allowing the coil part to output the static magnetic field and a time-varying magnetic field path portion allowing the coil part to output the time-varying magnetic field.

6 Claims, 10 Drawing Sheets

(51) Int. Cl.
    *H02M 3/158*     (2006.01)
    *H02M 7/48*     (2007.01)
    *A61B 34/00*     (2016.01)
    *A61B 17/00*     (2006.01)

(52) U.S. Cl.
    CPC ............... *A61B 2017/00345* (2013.01); *A61B 2017/00411* (2013.01); *A61B 2034/731* (2016.02); *H02M 2007/4815* (2013.01)

(58) Field of Classification Search
    USPC ........................................................ 307/104
    See application file for complete search history.

MICROROBOT PROPULSION APPARATUS BASED ON WIRELESS POWER TRANSFER INCLUDING MULTIPURPOSE INVERTER AND METHOD OF MANUFACTURING THE SAME

CROSS-REFERENCE TO RELATED APPLICATION

This application claims priority to Korean Patent Application No. 10-2017-0166206, filed on Dec. 5, 2017, and Korean Patent Application No. 10-2018-0073410, filed on Jun. 26, 2018, in the Korean Intellectual Property Office, the disclosures of each of which are incorporated herein by reference.

BACKGROUND OF THE DISCLOSURE

Field of the Disclosure

The present disclosure relates to a microrobot propulsion apparatus and a method of manufacturing the same, and more particularly, to a magnetic field generator for generating a time-varying magnetic field and a static magnetic field to supply wireless power and propulsive force to a microrobot.

Description of the Related Art

When a microrobot is inserted into a human body and operation thereof is wirelessly controlled for movement, power supply using a wireless power system is required.

Figure 1:
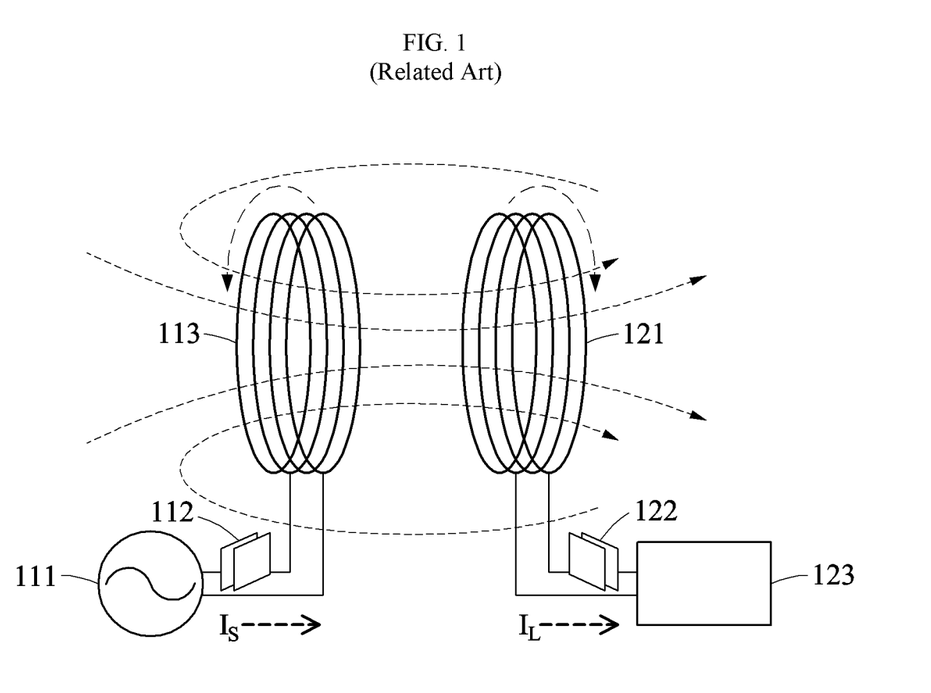
FIG. 1 is a drawing for explaining a wireless power system.

FIG. 1 is a drawing for explaining a wireless power system.

Referring to FIG. 1, the wireless power system may include a wireless power transmitter and a wireless power receiver.

In this case, the wireless power receiver may be a microrobot.

The microrobot may include a receiving coil 121, a capacitor 122, and a load 123.

The microrobot may receive wireless power signals from the wireless power transmitter through the receiving coil 121.

In the microrobot, the resonance frequency thereof may be matched with that of the wireless power transmitter by the capacitor 122, so that the transmission efficiency of wireless power may be maximized.

The wireless power transmitter may include a power source 111, a capacitor 112, and a transmitting coil 113.

The transmitting coil 113 may receive energy from the power source 111 by electric current $I_S$ and transmit wireless power signals to the microrobot.

The capacitor 112 may determine the resonance frequency of the wireless power signal transmitted by the transmitting coil 113.

Therefore, the wireless power transmitter may supply energy to the microrobot by generating a time-varying magnetic field.

In addition, propulsive force is required to move the microrobot in the human body.

An electromagnet may be used to supply the microrobot with propulsive force generated by the action of attractive and repulsive forces.

Figure 2:
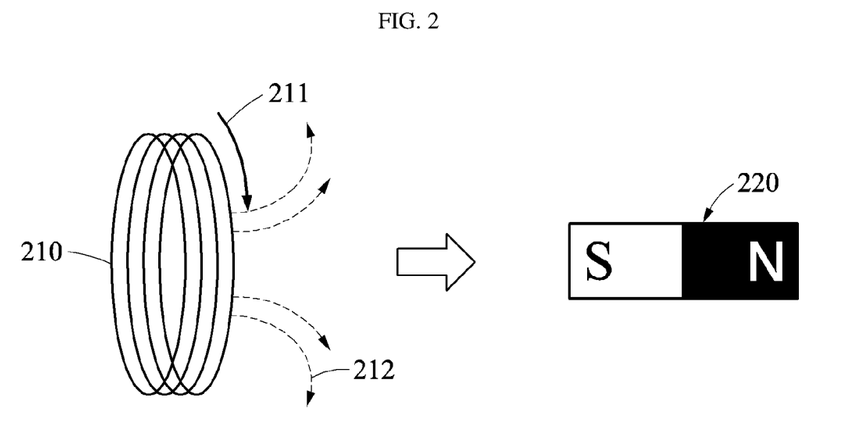
FIG. 2 is a drawing for explaining a microrobot capable of receiving propulsive force using an electromagnet.

FIG. 2 is a drawing for explaining a microrobot capable of receiving propulsive force using an electromagnet.

Referring to FIG. 2, the microrobot may be represented by a magnet 200 having S and N poles.

The electromagnet may include the power source 111 and a coil 210.

The coil 210 may be supplied with direct current energy from a power source, and the electric current 211 may flow therein.

The electric current 211 of the coil 210 may form a magnetic field 212.

The N pole of the magnetic field 212 is oriented toward a microrobot 220.

Therefore, by the magnetic field generated by the electromagnet, attractive force acting toward the electromagnet may be applied to the microrobot 220.

In addition, the electromagnet may reverse the direction of electric current to supply repulsive force to the microrobot.

As described above, the microrobot may receive power and propulsive force using the wireless power transmission system and the electromagnet. However, since the microrobot includes two types of devices, the manufacturing costs and volume of the microrobot may increase.

RELATED DOCUMENTS

Patent Documents

[Patent Document 1] Korean Patent Application Publication No. 10-2012-0116801, "WIRELESS POWER TRANSMISSION CIRCUIT AND WIRELESS POWER TRANSMITTER AND RECEIVER" (Oct. 23, 2012)

SUMMARY OF THE DISCLOSURE

Therefore, the present disclosure has been made in view of the above problems, and it is an object of the present disclosure to provide a microrobot propulsion apparatus capable of supplying both wireless power and propulsive force to a microrobot inserted into the human body.

It is another object of the present disclosure to provide a microrobot propulsion apparatus capable of generating a time-varying magnetic field to supply wireless power.

It is another object of the present disclosure to provide a microrobot propulsion apparatus capable of maximizing power transmission efficiency using a resonance frequency.

It is another object of the present disclosure to provide a microrobot propulsion apparatus capable of generating a static magnetic field to generate attractive and repulsive forces to provide propulsive force to a microrobot.

It is another object of the present disclosure to provide a microrobot propulsion apparatus that may be manufactured at low cost and that may supply wireless power and propulsive force to a microrobot.

It is yet another object of the present disclosure to provide a microrobot propulsion apparatus that may be miniaturized so as to be suitable for supplying wireless power and propulsive force to a microrobot.

In accordance with the present disclosure, the above and other objects can be accomplished by the provision of a microrobot propulsion apparatus based on wireless power transmission according to one embodiment of the present disclosure, including a coil part for outputting a time-varying magnetic field or a static magnetic field applied to a microrobot including a coil for receiving power and a coil for an electromagnet, and a multipurpose inverter including a static magnetic field path portion allowing the coil part to output the static magnetic field and a time-varying magnetic field path portion allowing the coil part to output the time-varying magnetic field.

In addition, the multipurpose inverter may include an H-bridge inverter having first and second direct-current ends respectively connected to first and second ends of an input power source; a capacitor having a first end connected to a second end of the coil part and a second end connected to a second alternating-current end of the H-bridge inverter; a first switch having a first end connected to a first end of the coil part and a second end connected to a second end of the input power source; and a second switch having a first end connected to a first end of the input power source and a second end connected to a second end of the coil part.

In addition, the H-bridge inverter may include a third switch having a first end connected to a first end of the input power source and a second end connected to a first end of the coil part; a fourth switch having a first end connected to a second end of the capacitor and a second end connected to a second end of the input power source; a fifth switch having a first end connected to a first end of the input power source and a second end connected to a second end of the capacitor; and a sixth switch having a first end connected to a first end of the coil part and a second end connected to a second end of the input power source.

In addition, the microrobot propulsion apparatus may further include a control part for turning the first to sixth switches on or off so that the coil part outputs the static magnetic field or the time-varying magnetic field.

In addition, the static magnetic field path portion may include a first switch having a first end connected to a first end of an input power source and a second end connected to a second end of the coil part; and a second switch having a first end connected to a first end of the coil part and a second end connected to a second end of the input power source.

In addition, the time-varying magnetic field path portion may include a third switch having a first end connected to a first end of the input power source and a second end connected to a first end of the coil part; a capacitor having a first end connected to a second end of the coil part; a fourth switch having a first end connected to a second end of the capacitor and a second end connected to a second end of the input power source; a fifth switch having a first end connected to a first end of the input power source and a second end connected to a second end of the capacitor; and a sixth switch having a first end connected to a first end of the coil part and a second end connected to a second end of the input power source.

In addition, the microrobot propulsion apparatus may further include a control part for turning the first to sixth switches on or off so that the coil part generates the static magnetic field or the time-varying magnetic field.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

The present disclosure will now be described more fully with reference to the accompanying drawings and contents disclosed in the drawings. However, the present disclosure should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context. It will be further understood that the terms "comprise" and/or "comprising", when used in this specification, specify the presence of stated components, steps, operations, and/or elements, but do not preclude the presence or addition of one or more other components, steps, operations, and/or elements thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the disclosure and the appended claims, the singular forms "a", "an" and "the" are intended to include the plural forms as well, unless context clearly indicates otherwise.

In addition, the terms such as "first" and "second" are used herein merely to describe a variety of constituent elements, but the constituent elements are not limited by the terms. The terms are used only for the purpose of distinguishing one constituent element from another constituent element.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In addition, in the following description of the present disclosure, a detailed description of known functions and configurations incorporated herein will be omitted when it may make the subject matter of the present disclosure unclear. The terms used in the specification are defined in consideration of functions used in the present disclosure, and can be changed according to the intent or conventionally used methods of clients, operators, and users. Accordingly, definitions of the terms should be understood on the basis of the entire description of the present specification.

Figure 3:
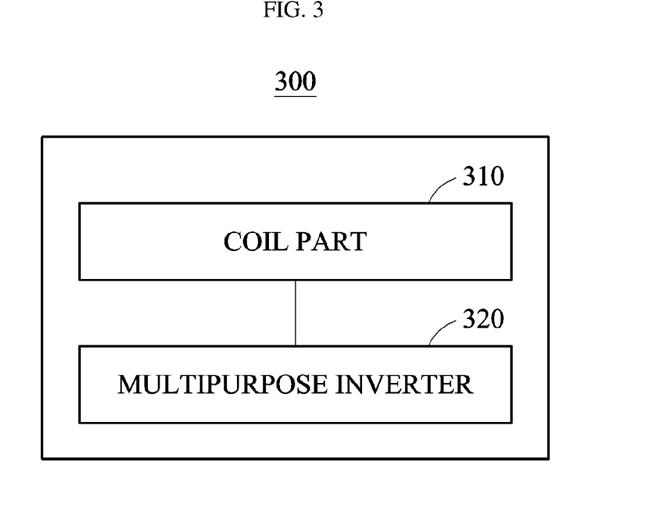
FIG. 3 is a block diagram of a microrobot propulsion apparatus based on wireless power transmission according to one embodiment of the present disclosure.

FIG. 3 is a block diagram of a microrobot propulsion apparatus based on wireless power transmission according to one embodiment of the present disclosure.

In this specification, the microrobot propulsion apparatus based on wireless power transmission may be simply referred to as a 'magnetic field generator'.

Referring to FIG. 3, the magnetic field generator 300 may include a coil part 310 and a multipurpose inverter 320.

The coil part 310 may output a time-varying magnetic field or a static magnetic field applied to the microrobot including a coil for receiving power and a coil for an electromagnet.

The coil part 310 may be an inductor.

The intensity of the time-varying magnetic field may vary over time.

The time-varying magnetic field may be a wireless power signal.

The microrobot may receive energy by the time-varying magnetic field.

The intensity of the static magnetic field may not vary over time.

The microrobot may obtain propulsive force through the static magnetic field.

The direction of the static magnetic field may be changed as needed.

For example, when the microrobot requires an attractive force, the magnetic field generator 300 may output a static magnetic field in the direction opposite to the static magnetic field of the microrobot.

When the microrobot requires a repulsive force, the magnetic field generator 300 may output a static magnetic field in the same direction as the static magnetic field of the microrobot.

The microrobot may include a coil for receiving power and a coil for an electromagnet.

The coil for receiving power may receive a time-varying magnetic field from the magnetic field generator 300 to receive energy.

The microrobot may generate a static magnetic field using the coil for an electromagnet.

The coil for an electromagnet may change the direction of the static magnetic field depending on force required by the microrobot.

The microrobot may obtain an attractive or repulsive force by the static magnetic field output from the magnetic field generator 300.

The multipurpose inverter 320 may include a static magnetic field path portion allowing the coil part 310 to output a static magnetic field and a time-varying magnetic field path portion allowing the coil part 310 to output a time-varying magnetic field.

The static magnetic field path portion may include a first switch having a first end connected to a first end of an input power source and a second end connected to a second end of the coil part, and a second switch having a first end connected to a second end of the coil part and a second end connected to a second end of the input power source.

The time-varying magnetic field path portion may include a third switch having a first end connected to a first end of the input power source and a second end connected to a first end of a coil part 410, a capacitor having a first end connected to a second end of the coil part, a fourth switch having a first end connected to a second end of the capacitor and a second end connected to a second end of the input power source, a fifth switch having a first end connected to a first end of the input power source and a second end connected to a second end of the capacitor and having a first end connected to a first end of the coil part and a second end connected to a second end of the input power source.

The multipurpose inverter 320 may include an H-bridge inverter having first and second direct-current ends respectively connected to first and second ends of the input power source, a capacitor having a first end connected to a second end of the coil part 310 and a second end connected to a second alternating-current end of the H-bridge inverter, a first switch having a first end connected to a first end of the coil part 310 and a second end connected to a second end of the input power source, and a second switch having a second end connected to a second end of the coil part 310.

The H-bridge inverter may include a third switch having a first end connected to a first end of the input power source and a second end connected to a first end of the coil part 310, a fourth switch having a first end connected to a second end of the capacitor and a second end connected to a second end of the input power source, a fifth switch having a first end connected to a first end of the input power source and a second end connected to a second end of the capacitor, and a sixth switch having a first end connected to a first end of the coil part and a second end connected to a second end of the input power source.

The magnetic field generator 300 according to one embodiment of the present disclosure may further include a control part (not shown).

The control part may turn the first to sixth switches on or off so that the coil part 310 may output a static magnetic field or a time-varying magnetic field.

In addition, the control part may control the intensity of the static magnetic field generated in the magnetic field generator 300 to control the intensity of the propulsive force of the microrobot.

Figure 4:
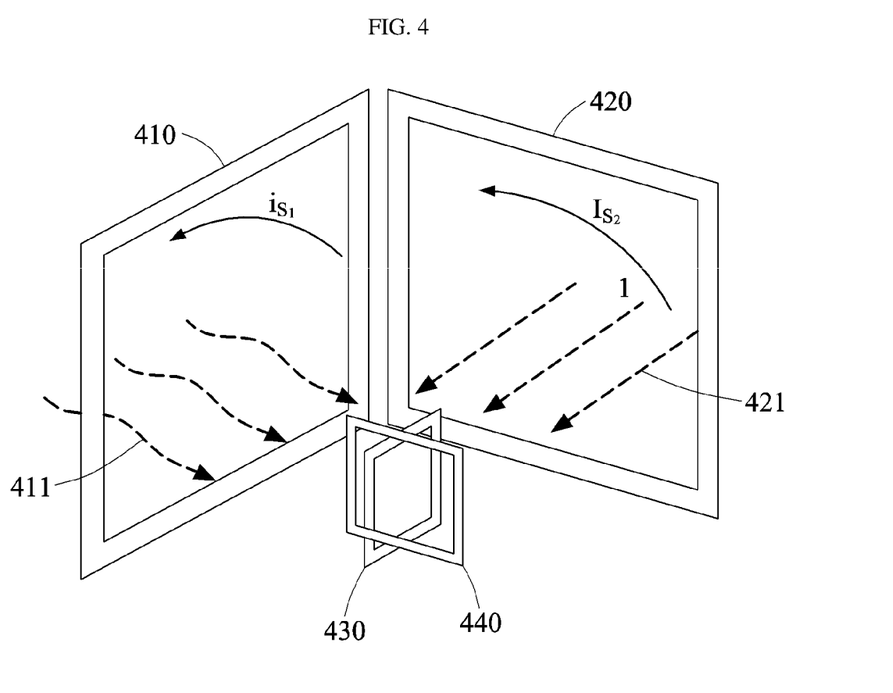
FIG. 4 is a drawing showing a magnetic field generator and a microrobot according to one embodiment of the present disclosure.

FIG. 4 is a drawing showing a magnetic field generator and a microrobot according to one embodiment of the present disclosure.

Referring to FIG. 4, the magnetic field generator may include first and second coil parts 410 and 420 and a power source (not shown).

The magnetic field generator may be supplied with energy from the power source.

Alternating current $I_{S2}$ may flow along the first coil part 410 by the power source.

The alternating current $I_{S2}$ may generate a time-varying magnetic field 411.

Direct current $I_{S1}$ may flow along the second coil part 420 by the power source.

The direct current $I_{S1}$ may generate a first static magnetic field 421.

In this case, the direction of the direct current $I_{S1}$ may be changed.

The microrobot may include a coil for receiving power 430, a coil for an electromagnet 440, and an inverter (not shown).

The coil for receiving power 430 and the coil for an electromagnet 440 may be arranged to be orthogonal to each other.

With this arrangement, interference between signals respectively received at the coil for receiving power 430 and the coil for an electromagnet 440 may be minimized.

In this case, the first coil part 410 of the magnetic field generator may be arranged to be parallel to the coil for receiving power 430.

In addition, the second coil part 420 of the magnetic field generator may be arranged to be parallel to the coil for an electromagnet 440.

That is, the first and second coil parts 410 and 420 may be arranged to be parallel to the receiving coils 430 and 440 of the microrobot to maximize transmission efficiency.

The coil for receiving power 430 may receive energy by the time-varying magnetic field 411.

The inverter may convert some of the received energy into constant electric current.

The coil for an electromagnet 440 may generate a second static magnetic field by the constant electric current.

Therefore, the microrobot may obtain an attractive or repulsive force depending on the direction of a first static magnetic field 420 generated in the magnetic field generator.

In addition, depending on the positions of the coil for receiving power 430 and the coil for an electromagnet 440 of the microrobot, the first coil part 410 may generate a static magnetic field and the second coil part 410 may generate a time-varying magnetic field.

In addition, the first and second coil parts 410 and 420 may be moved to other positions than the positions shown in FIG. 4 depending on the position of the microrobot.

In addition, the magnetic field generator may supply wireless power and propulsive force to the microrobot using only one of the first and second coil parts 410 and 420.

In addition, the magnetic field generator may supply wireless power and propulsive force to the microrobot using three or more coil parts.

In addition, the coil part or the coil parts may be moved to other positions depending on the position of the microrobot.

That is, the microrobot may be supplied with wireless power and propulsive force by the magnetic field generator.

Hereinafter, the configuration and operation of a magnetic field generator for supplying wireless power and propulsive force to a microrobot using one coil will be described with reference to FIGS. 5 to 9.

Figure 5:
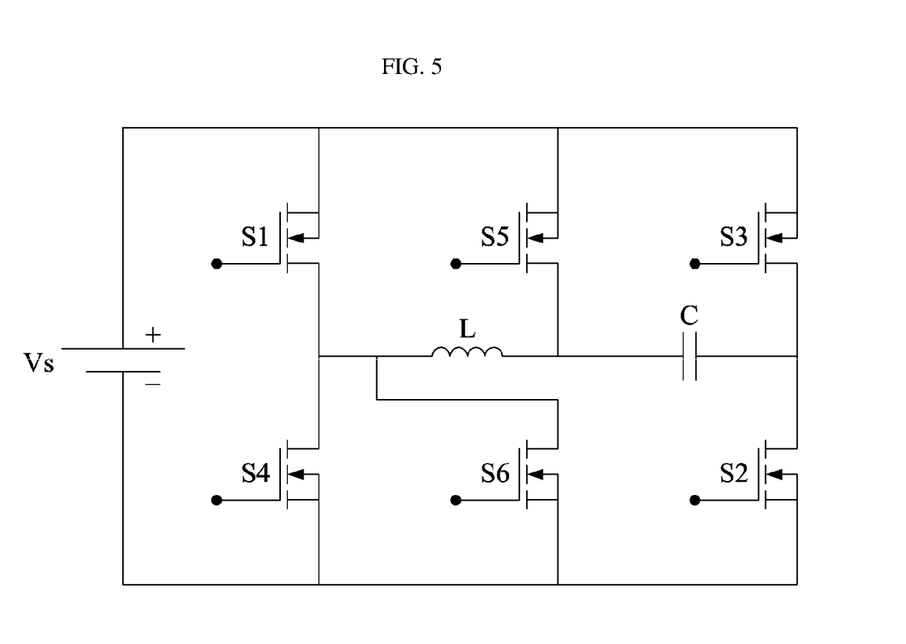
FIG. 5 is a circuit diagram of a magnetic field generator according to another embodiment of the present disclosure.

FIG. 5 is a circuit diagram of a magnetic field generator according to another embodiment of the present disclosure.

Referring to FIG. 5, the magnetic field generator may include a coil part and path portions.

The coil part may be an inductor L.

The path portions may include a time-varying magnetic field path portion and a static magnetic field path portion.

The static magnetic field path portion may include a first switch S5 and a second switch S6.

The time-varying magnetic field path portion may include a capacitor C and third, fourth, fifth, and sixth switches S1, S2, S3, and S4.

An H-bridge circuit may include the third, fourth, fifth, and sixth switches S1, S2, S3, and S4.

The first to sixth switches S1, S2, S3, S4, S5 and S6 may be metal oxide semiconductor field effect transistors (MOSFETs).

The inductance of an inductor L and the capacitance of the capacitor C may determine the resonance frequency of the time-varying magnetic field.

That is, the resonance frequency may be determined by adjusting the capacitance.

The first to sixth switches S1, S2, S3, S4, S5 and S6 may be n-channel MOSFETs.

In The first to sixth switches S1, S2, S3, S4, S5 and S6, a first end may be a drain end, a second end may be a source end, and a third end may be a gate end.

The first to sixth switches S1, S2, S3, S4, S5 and S6 may receive control signals through the gate end by the control part.

S1 may have a first end connected to a first end of an input power source $V_S$ and a second end connected to a first end of L.

The input power source $V_S$ may be a direct-current voltage power source.

A first end of the input power source may be a positive electrode, and a second end of the input power source may be a negative electrode.

C may have a first end connected to a second end of L.

S2 may have a first end connected to a second end of C and a second end connected to a second end of $V_S$.

S3 may have a first end connected to a first end of $V_S$ and a second end connected to a second end of C.

S4 may have a first end connected to a first end of L and a second end connected to a second end of $V_S$.

S5 may have a first end connected to a first end of $V_S$ and a second end connected to a second end of L.

S6 may have a first end connected to a first end of L and a second end connected to a second end of $V_S$.

Figure 6A:
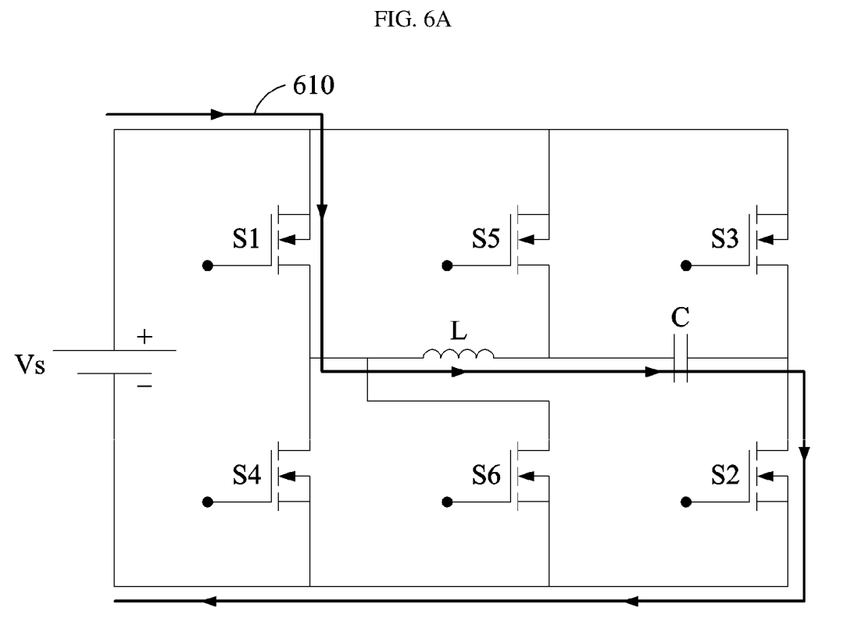
FIGS. 6A and 6B are drawings for explaining a process by which the time-varying magnetic field of the magnetic field generator shown in FIG. 5 is generated.
Figure 6B:
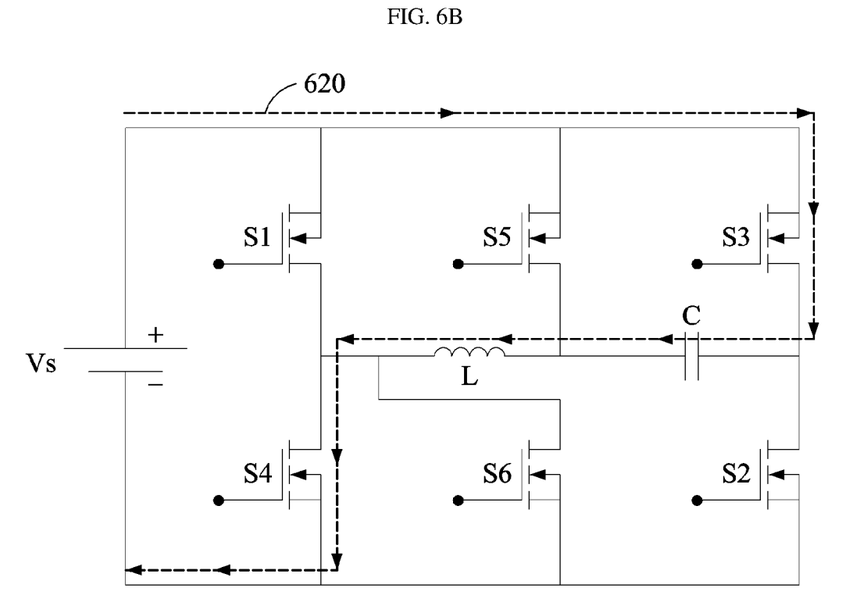

FIGS. 6A and 6B are drawings for explaining a process by which the time-varying magnetic field of the magnetic field generator shown in FIG. 5 is generated.

Figure 7:
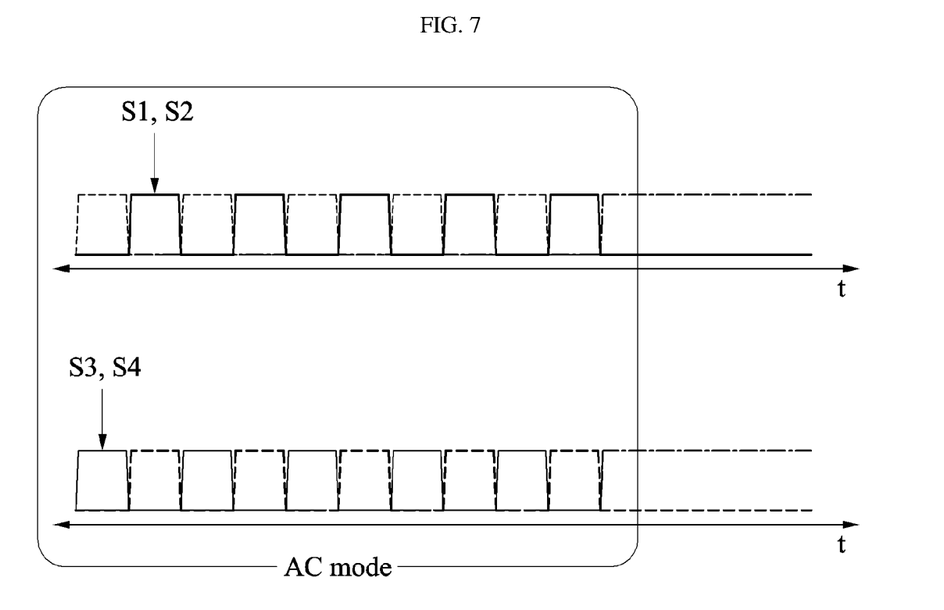
FIG. 7 is a drawing showing control signals applied to switches in the process of generating a time-varying magnetic field.

FIG. 7 is a drawing showing control signals applied to switches in the process of generating a time-varying magnetic field.

Referring to FIGS. 6A and 6B and FIG. 7, the magnetic field generator may form paths for a first electric current 610 and a second electric current 620 to generate the time-varying magnetic field.

The input power source $V_S$ may supply a direct-current voltage.

The control part may output control signals in an alternating current (AC) mode.

First, the control part may output the control signals to turn on S1 and S2 and turn off S3, S4, S5, and S6.

The first electric current 610 may be formed along S1, L, C, and S2.

In this case, L may form a first magnetic field by the first electric current 610.

Next, the control part may turn on S3 and S4, and may turn off S1, S2, S5, and S6.

The second electric current 620 may be formed along S3, C, L, and S4.

In this case, L may form a second magnetic field in a direction opposite to the direction of the first magnetic field by the second electric current 620.

Therefore, in the magnetic field generator 300 shown in FIG. 3, formation of the first electric current 610 and the second electric current 620 may be repeated to output the time-varying magnetic field.

Figure 8:
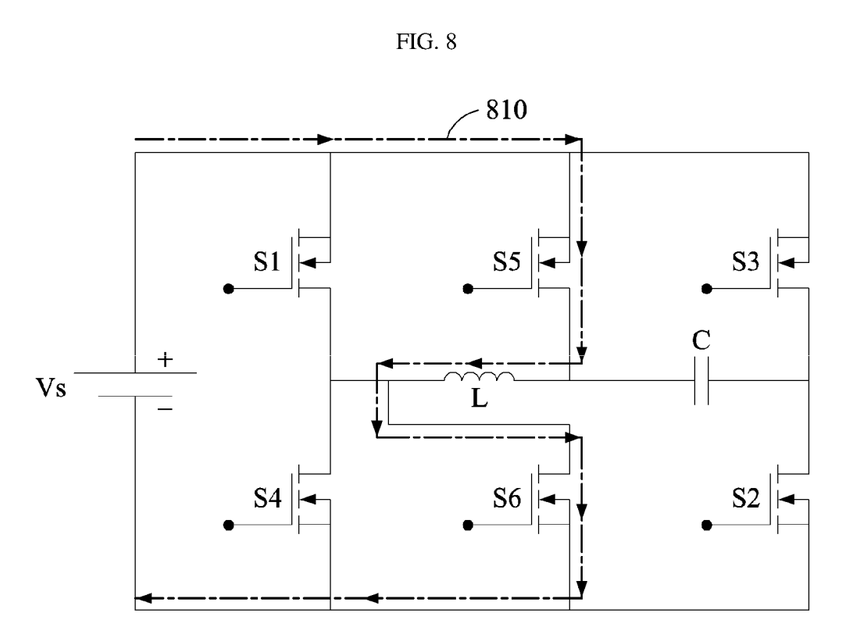
FIG. 8 is a drawing for explaining a process by which the static magnetic field of the magnetic field generator shown in FIG. 5 is generated.

FIG. 8 is a drawing for explaining a process by which the static magnetic field of the magnetic field generator shown in FIG. 5 is generated.

Figure 9:
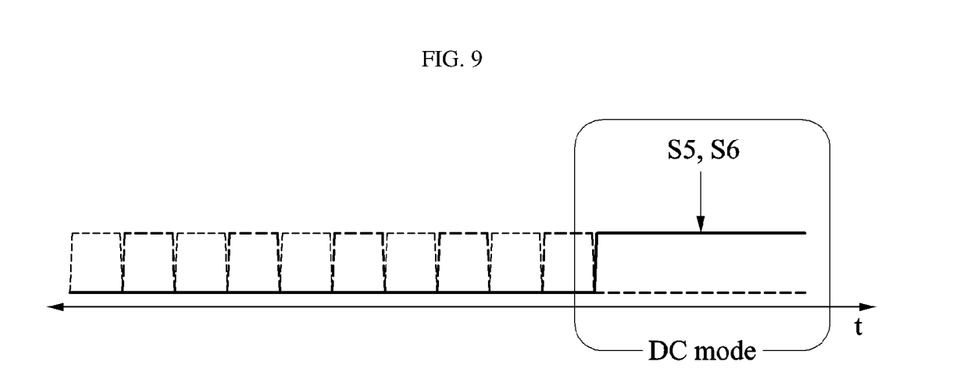
FIG. 9 is a drawing showing control signals applied to switches in the process of generating a static magnetic field.

FIG. 9 is a drawing showing control signals applied to switches in the process of generating a static magnetic field.

Referring to FIGS. 8 and 9, the magnetic field generator may form a third electric current to generate a time-varying magnetic field.

The input power source $V_S$ may supply a direct-current voltage.

The control part may output control signals in a direct current (DC) mode.

The control part may turn on S5 and S6, and may turn off S1, S2, S3, and S4 by the control signals.

A third electric current 810 may be formed along S5, L, and S6.

In this case, L may form a third magnetic field by the third electric current 810.

Therefore, the magnetic field generator 300 shown in FIG. 3 may output a static magnetic field by the third electric current 810.

Therefore, the magnetic field generator 300 shown in FIG. 3 may supply the time-varying magnetic field and the static magnetic field to supply wireless power and propulsive force to a microrobot.

The microrobot propulsion apparatus according to one embodiment of the present disclosure can supply wireless power and propulsive force to a microrobot inserted into the human body.

The microrobot propulsion apparatus according to one embodiment of the present disclosure can generate a time-varying magnetic field to supply wireless power.

The microrobot propulsion apparatus according to one embodiment of the present disclosure can maximize power transmission efficiency using a resonance frequency.

The microrobot propulsion apparatus according to one embodiment of the present disclosure can generate a static magnetic field to generate attractive and repulsive forces to provide propulsive force to a microrobot.

The microrobot propulsion apparatus according to one embodiment of the present disclosure can be manufactured at low cost and can supply wireless power and propulsive force to a microrobot.

The microrobot propulsion apparatus according to one embodiment of the present disclosure can be miniaturized so as to be suitable for supplying wireless power and propulsive force to a microrobot.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and one or more software applications executing on the operating system. In addition, the processing device may access, store, manipulate, process, and generate data in response to execution of the software. For ease of understanding, the processing apparatus may be described as being used singly, but those skilled in the art will recognize that the processing apparatus may include a plurality of processing elements and/or a plurality of types of processing elements. For example, the processing apparatus may include a plurality of processors or one processor and one controller. Other processing configurations, such as a parallel processor, are also possible.

The software may include computer programs, code, instructions, or a combination of one or more of the foregoing, configure the processing apparatus to operate as desired, or command the processing apparatus, either independently or collectively. In order to be interpreted by a processing device or to provide instructions or data to a processing device, the software and/or data may be embodied permanently or temporarily in any type of a machine, a component, a physical device, a virtual device, a computer storage medium or device, or a transmission signal wave. The software may be distributed over a networked computer system and stored or executed in a distributed manner. The software and data may be stored in one or more computer-readable recording media.

The methods according to the embodiments of the present disclosure may be implemented in the form of a program command that can be executed through various computer means and recorded in a computer-readable medium. The computer-readable medium can store program commands, data files, data structures or combinations thereof. The program commands recorded in the medium may be specially designed and configured for the present disclosure or be known to those skilled in the field of computer software. Examples of a computer-readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands. Examples of the program commands include machine language code created by a compiler and high-level language code executable by a computer using an interpreter and the like. The hardware devices described above may be configured to operate as one or more software modules to perform the operations of the embodiments, and vice versa.

Although the present disclosure has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

What is claimed is:

1. A microrobot propulsion apparatus based on wireless power transmission, comprising:
   a coil part configured to output a time-varying magnetic field or a static magnetic field applied to a microrobot comprising a coil for receiving power and a coil for an electromagnet; and
   a multipurpose inverter comprising a static magnetic field path portion allowing the coil part to output the static magnetic field and a time-varying magnetic field path portion allowing the coil part to output the time-varying magnetic field,
   wherein the multipurpose inverter comprises:
   an H-bridge inverter having first and second direct-current ends respectively connected to first and second ends of an input power source,
   a capacitor having a first end connected to a second end of the coil part and a second end connected to a second alternating-current end of the H-bridge inverter,
   a first switch having a first end connected to a first end of the coil part and a second end connected to a second end of the input power source, and
   a second switch having a first end connected to a first end of the input power source and a second end connected to a second end of the coil part.

2. The microrobot propulsion apparatus according to claim 1, wherein the H-bridge inverter comprises a third switch having a first end connected to a first end of the input power source and a second end connected to a first end of the coil part;
a fourth switch having a first end connected to a second end of the capacitor and a second end connected to a second end of the input power source;
a fifth switch having a first end connected to a first end of the input power source and a second end connected to a second end of the capacitor; and
a sixth switch having a first end connected to a first end of the coil part and a second end connected to a second end of the input power source.

3. The microrobot propulsion apparatus according to claim 2, further comprising:
a control part configured to turn the first to sixth switches on or off so that the coil part outputs the static magnetic field or the time-varying magnetic field.

4. The microrobot propulsion apparatus according to claim 1, wherein the static magnetic field path portion comprises a first switch having a first end connected to a first end of an input power source and a second end connected to a second end of the coil part; and
a second switch having a first end connected to a first end of the coil part and a second end connected to a second end of the input power source.

5. A microrobot propulsion apparatus based on wireless power transmission, comprising:
a coil part configured to output a time-varying magnetic field or a static magnetic field applied to a microrobot comprising a coil for receiving power and a coil for an electromagnet; and
a multipurpose inverter comprising a static magnetic field path portion allowing the coil part to output the static magnetic field and a time-varying magnetic field path portion allowing the coil part to output the time-varying magnetic field,
wherein the static magnetic field path portion comprises:
a first switch having a first end connected to a first end of an input power source and a second end connected to a second end of the coil part; and
a second switch having a first end connected to a first end of the coil part and a second end connected to a second end of the input power source, and
wherein the time-varying magnetic field path portion comprises a third switch having a first end connected to a first end of the input power source and a second end connected to a first end of the coil part;
a capacitor having a first end connected to a second end of the coil part;
a fourth switch having a first end connected to a second end of the capacitor and a second end connected to a second end of the input power source;
a fifth switch having a first end connected to a first end of the input power source and a second end connected to a second end of the capacitor; and
a sixth switch having a first end connected to a first end of the coil part and a second end connected to a second end of the input power source.

6. The microrobot propulsion apparatus according to claim 5, further comprising:
a control part configured to turn the first to sixth switches on or off so that the coil part generates the static magnetic field or the time-varying magnetic field.

* * * * *